(12) United States Patent
Zafar et al.

(10) Patent No.: US 12,368,024 B2
(45) Date of Patent: Jul. 22, 2025

(54) METHODS AND APPARATUS FOR PROCESSING A SUBSTRATE

(71) Applicant: Applied Materials, Inc., Santa Clara, CA (US)

(72) Inventors: Abdullah Zafar, Santa Clara, CA (US); William John Durand, Oakland, CA (US); Xinyuan Chong, Milpitas, CA (US); Kenric Choi, San Jose, CA (US); Weize Hu, Sunnyvale, CA (US); Kelvin Chan, San Ramon, CA (US); Amir Bayati, San Jose, CA (US); Michelle Sanpedro, Mountain View, CA (US); Philip A. Kraus, San Jose, CA (US); Adolph Miller Allen, Oakland, CA (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 799 days.

(21) Appl. No.: 17/496,427

(22) Filed: Oct. 7, 2021

(65) Prior Publication Data

US 2022/0328285 A1 Oct. 13, 2022

Related U.S. Application Data

(60) Provisional application No. 63/173,270, filed on Apr. 9, 2021.

(51) Int. Cl.
*C23C 16/52* (2006.01)
*C23C 16/455* (2006.01)
(Continued)

(52) U.S. Cl.
CPC .... *H01J 37/3244* (2013.01); *C23C 16/45512* (2013.01); *C23C 16/45544* (2013.01);
(Continued)

(58) Field of Classification Search
None
See application file for complete search history.

(56) References Cited

U.S. PATENT DOCUMENTS 5,146,294 A * 9/1992 Grisar ............... G01N 21/39
250/341.5
5,534,066 A 7/1996 O'Neill et al.
(Continued)

OTHER PUBLICATIONS

PCT International Search Report and Written Opinion for PCT/US2022/019528 dated Jun. 24, 2022.

*Primary Examiner* — Charles Capozzi
(74) *Attorney, Agent, or Firm* — Moser Taboada

(57) ABSTRACT

Methods and apparatus for processing a substrate are provided herein. For example, a gas supply configured for use with a processing chamber includes an ampoule that stores a precursor and comprises an input to receive a carrier gas and an output to provide a mixture of the carrier gas and the precursor to the processing chamber and a sensor assembly comprising a detector and an infrared source operably connected to an outside of an enclosure, through which the mixture flows, and a gas measurement volume disposed within the enclosure and along an inner wall thereof so that a concentration of the precursor in the mixture can be measured by the detector and transmitted to a controller.

17 Claims, 4 Drawing Sheets

(51) Int. Cl.
*G01N 21/3504* (2014.01)
*G01N 33/00* (2006.01)
*H01J 37/32* (2006.01)

(52) U.S. Cl.
CPC ........ *C23C 16/45553* (2013.01); *C23C 16/52* (2013.01); *G01N 21/3504* (2013.01); *G01N 33/0027* (2013.01); *H01J 37/3299* (2013.01); *H01J 2237/24585* (2013.01); *H01J 2237/332* (2013.01)

(56) References Cited

U.S. PATENT DOCUMENTS

| | | |
|---|---|---|
| 9,399,575 B2 | 7/2016 | Lichty et al. |
| 10,443,127 B2 | 10/2019 | Hsieh et al. |
| 2004/0018746 A1 | 1/2004 | Arno |
| 2007/0048181 A1 | 3/2007 | Chang et al. |
| 2008/0044573 A1 | 2/2008 | Chen et al. |
| 2019/0120754 A1* | 4/2019 | Schossig ............... G01N 21/031 |
| 2019/0264324 A1 | 8/2019 | Shugrue et al. |
| 2020/0041407 A1 | 2/2020 | Huang et al. |
| 2020/0386677 A1 | 12/2020 | Deliwala |
| 2022/0236173 A1* | 7/2022 | Nikittin ................. G01N 21/05 |

* cited by examiner

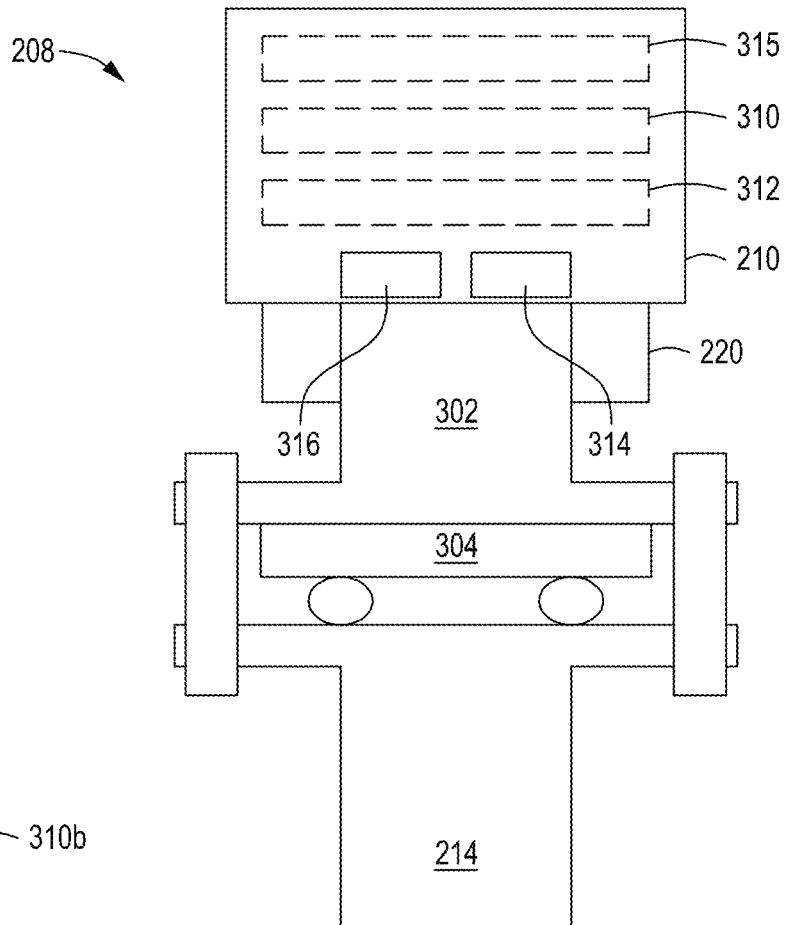
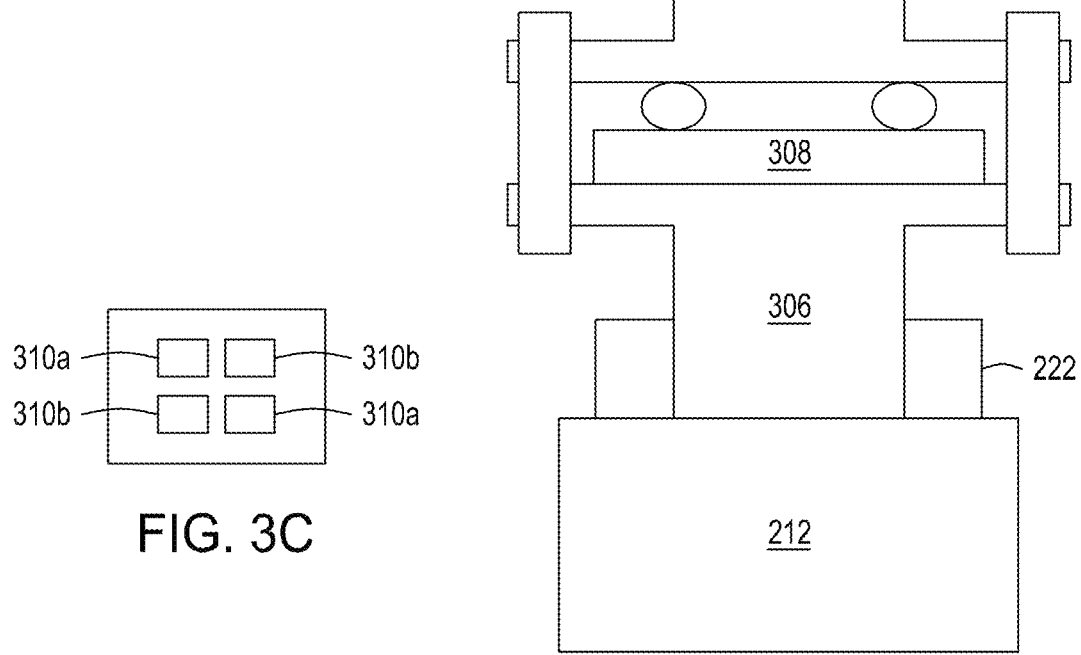
FIG. 3B
FIG. 3C
FIG. 3A

METHODS AND APPARATUS FOR PROCESSING A SUBSTRATE

CROSS-REFERENCE TO RELATED APPLICATIONS

The present application claims the benefit of and priority to U.S. Provisional Patent Application Ser. No. 63/173,270, which was filed on Apr. 9, 2021, the entire contents of which is incorporated herein by reference.

FIELD

Embodiments of the present disclosure generally relate to methods and apparatus for processing a substrate, and more particularly, to methods and apparatus comprising integrated high accuracy non-dispersive infrared (NDIR) sensor assembly for substrate processing.

BACKGROUND

Methods and apparatus for processing a substrate are known. For example, in some instances processing chambers can be configured to develop film properties on one or more layers of a substrate (e.g., a metal layer, such as tantalum nitride (TaN) barrier). Typically, one or more precursors are introduced into the processing chamber (e.g., chemical vapor deposition (CVD), atomic layer deposition (ALD), etc.). During a precursor phase of substrate processing, gas concentration sensing is desired to determine an amount of a precursor delivered to the substrate. Typically, the precursor is pushed from an ampoule of a gas supply to the processing chamber by an inert carrier gas (e.g., argon, or other noble gas). Current sensor technology uses a sensor located downstream from the ampoule (e.g., in an enclosure (typically referred to as a hot can due to the high temperatures therein)) to measure an absolute gas concentration level, which can be on the order of 0.2%. Current sensor technology, however, is insufficient for process control, as such technology is only capable of an accuracy of about +/−2.5% of the absolute gas concentration level. That is, the high temperatures in the enclosure cause excessive noise and decreases an SNR of conventional sensors.

SUMMARY

Methods and apparatus for processing a substrate are provided herein. For example, a gas supply configured for use with a processing chamber includes an ampoule that stores a precursor and comprises an input to receive a carrier gas and an output to provide a mixture of the carrier gas and the precursor to the processing chamber and a sensor assembly comprising a detector and an infrared source operably connected to an outside of an enclosure, through which the mixture flows, and a gas measurement volume disposed within the enclosure and along an inner wall thereof so that a concentration of the precursor in the mixture can be measured by the detector and transmitted to a controller.

In accordance with at least some embodiments of the present disclosure a gas supply configured for use with a processing chamber includes an ampoule that stores a precursor and comprises an input to receive a carrier gas and an output to provide a mixture of the carrier gas and the precursor to the processing chamber and a sensor assembly comprising a detector comprising a thermopile sensor or a pyroelectric sensor and an infrared source operably connected to an outside of an enclosure, through which the mixture flows, and a gas measurement volume disposed within the enclosure and extending parallel along an inner wall thereof so that a concentration of the precursor in the mixture can be measured by the detector and transmitted to a controller.

In accordance with at least some embodiments of the present disclosure a system for processing a substrate includes a processing chamber and a gas supply operably coupled to the processing chamber and comprising an ampoule that stores a precursor and comprises an input to receive a carrier gas and an output to provide a mixture of the carrier gas and the precursor to the processing chamber; and a sensor assembly comprising a detector operably connected to an outside of an enclosure and an infrared source disposed within the enclosure, through which the mixture flows, and a gas measurement volume disposed within the enclosure and extending along an inner wall thereof so that a concentration of the precursor in the mixture can be measured by the detector and transmitted to a controller.

In accordance with at least some embodiments of the present disclosure a method of processing a substrate includes supplying a carrier gas from a gas supply to an input of an ampoule that stores a precursor, supplying from an output of the ampoule a mixture of the carrier gas and the precursor to a sensor assembly comprising a detector and an infrared source operably connected to an outside of an enclosure, through which the mixture flows, and a gas measurement volume disposed within the enclosure and along an inner wall thereof so that a concentration of the precursor in the mixture can be measured by the detector and transmitted to a controller, determining the concentration of the precursor based on an equation: $C = CA/CB = (kB\ TNA\ \delta v / \Psi lP) \log 10\ (\phi 0/\phi)) \times 100\%$, where $C$=concentration of A in B [Abs], $C_A$=concentration of A [mol/m$^3$], $C_B$=concentration of B [mol/m$^3$], $K_B$=Boltzmann Constant [J/K], T=Temperature [K], $N_A$=Avogadro's Number [#/mol], $\Psi$=Integrated Molar Absorptivity [m/mol], l=IR Source Path Length, [m], P=Total Pressure [Pa], $\phi_0$=Photodiode Signal without A, $\phi$=Photodiode Signal with A, and $\delta v$=spectral width of filter [m$^{-1}$], and adjusting a temperature of the ampoule based on a determined concentration of the precursor.

Other and further embodiments of the present disclosure are described below.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

FIG. 3A is a diagram of a nondispersive infrared sensor, in accordance with at least some embodiments of the present disclosure.

FIG. 3B is a diagram of a detector configuration of the nondispersive infrared sensor, in accordance with at least some embodiments of the present disclosure.

FIG. 3C is a diagram of a detector configuration of the nondispersive infrared sensor, in accordance with at least some embodiments of the present disclosure.

Figure 1:
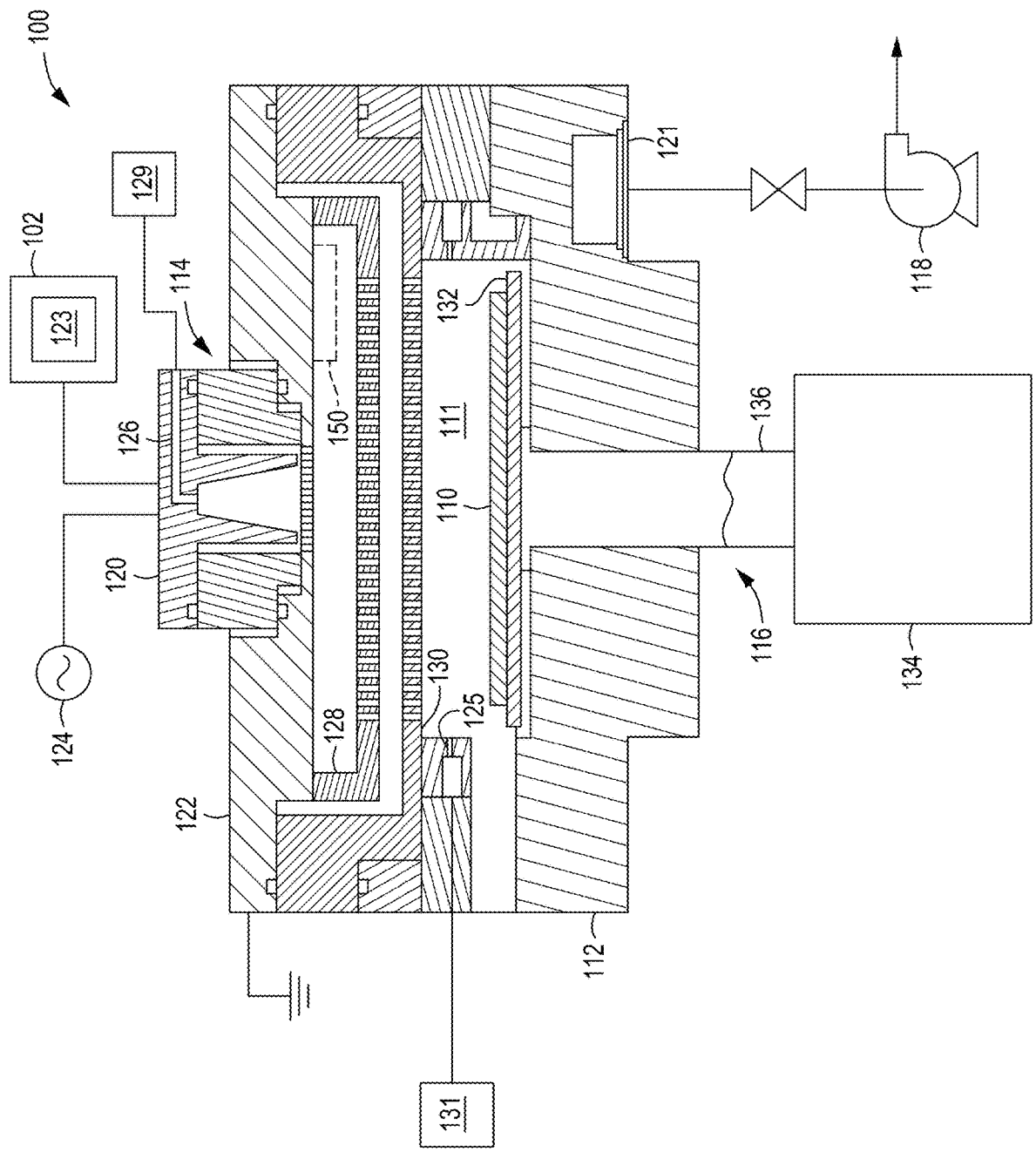
FIG. 1 is a schematic diagram of a processing chamber, in accordance with at least some embodiments of the present disclosure.

To facilitate understanding, identical reference numerals have been used, where possible, to designate identical elements that are common to the figures. The figures are not drawn to scale and may be simplified for clarity. Elements and features of one embodiment may be beneficially incorporated in other embodiments without further recitation.

DETAILED DESCRIPTION

Embodiments of methods and apparatus for processing a substrate are provided herein. For example, methods and apparatus described herein use a sensor assembly comprising a detector and an infrared source operably connected to an outside of an enclosure (e.g., a hot can). A gas measurement volume of the sensor assembly is disposed within the enclosure and along an inner wall thereof so that a concentration of the precursor in the mixture can be measured by the detector and transmitted to a controller during substrate processing. The sensor assembly can be a non-dispersive infrared sensor assembly (NDIR sensor assembly) that is configured to directly measure a concentration of a precursor contained in a carrier gas (e.g., background of precursor contained in the carrier gas). Compared to conventional sensor technology, by moving the detector of the NDIR outside of the enclosure (e.g., to a reduced temperature location) and increasing the gas measurement volume (e.g., by increasing absorption measurement volume), noise attributed to the detector is greatly reduced and detector accuracy is greatly increased (e.g., up to five (5) times greater when compared to conventional sensor technology).

FIG. 1 is a cross sectional side view of a processing chamber 100 in accordance with at least some embodiments of the present disclosure. The processing chamber 100 is configured to perform one or more processes on a substrate 110. For example, in some embodiments, the processing chamber 100 can be a chemical vapor deposition chamber (CVD) configured to perform a CVD process, an atomic layer deposition chamber (ALD) configured to perform an ALD process, a clean or preclean chamber configured to perform a cleaning or preclean process, and/or an etch chamber configured to perform an etching process on a substrate. For example, the processing chamber 100 can be configured for performing ALD when processing the substrate 110. Apparatus that can be configured for performing a cleaning or an etch process with the NDIR sensor assembly described herein can be one of the deposition chambers available from Applied Materials, Inc. located in Santa Clara CA. Other apparatus available from Applied Materials, Inc., as well as those available from other manufacturers, may also be modified in accordance with the teachings disclosed herein. Such apparatus can be stand-alone apparatus, or one or more of the apparatus can be combined in a cluster tool.

Although the process chamber 100 may be configured for processing a substrate using other technique as disclosed herein, for illustrative purposes, the processing chamber 100 is assumed to be configured to perform an ALD process. Accordingly, in some embodiments, the processing chamber 100 includes a chamber body 112, a lid assembly 114, and a support assembly 116. The lid assembly 114 is disposed at an upper end of the chamber body 112, and the support assembly 116 is at least partially disposed within an inner volume 111 defined within the chamber body 112. A vacuum system can be used to evacuate/remove process gases from processing chamber 100 and can includes a vacuum pump 118 coupled to a vacuum port 121 disposed in the chamber body 112.

The processing chamber 100 also includes or is in communication with a controller 102 (or processor) for controlling processes within the processing chamber 100. The controller 102 includes a memory 123 (a non-transitory computer readable storage medium) having stored thereon instructions that when executed cause the controller 102 to perform a method for processing the substrate 110, including any of the methods disclosed herein. For example, in some embodiments, the controller 102 can be configured or programmed to tune an IR light source to one or more frequencies corresponding to various precursors present in a gas mixture that is being provided to the processing chamber 100 during operation, as will be described in greater detail below.

The lid assembly 114 includes at least two stacked components configured to form a plasma volume or cavity. A first electrode 120 is disposed vertically above a second electrode 122 to define a plasma volume. The first electrode 120 is connected to a power source 124 (e.g., a radio frequency (RF) power supply and/or a DC power supply), and the second electrode 122 is connected to ground or a reference potential, forming a capacitance between the first electrode 120 and the second electrode 122.

The lid assembly 114 also includes one or more gas inlets 126 to which a gas supply 129 can be coupled for providing the process gas (e.g., a mixture of carrier gas and precursor) to a surface of the substrate 110 through a blocker plate 128 and a gas distribution plate 130, such as a showerhead. In at least some embodiments, the process gas may use radicals of a plasma formed from one or more suitable process gases. For example, in some embodiments the process gas can include, but is not limited to, hydrogen ($H_2$), helium (He), an inert gas such as argon (Ar) (or other noble gas), ammonia ($NH_3$), water ($H_2O$), a fluorine containing gas such as nitrogen trifluoride ($NF_3$), hydrogen fluoride (HF), silicon tetrafluoride ($SiF_4$), one or more precursors, or any combination of these gases. For example, the precursors can include alkylamide precursors including, but not limited to, pentakis (dimethylamino) tantalum (V)—Ta $(NMe_2)_5$, typically referred to as PDMAT, titanium dioxide-tetrakis (dimethylamino) titanium ($C_8H_{24}N_4Ti$), typically referred to as TDMAT), $Al(C_2H_5)_3$, $AlEt_3$, $B_2H_6$, CCTBA, $CH_3C(O)N(CH_3)_2$ (DMA), $C_3H_8$ (propane), CO (carbon monoxide), Ru(EtCp)2, Ru(EtCp)2, $SiF_4$, $SiH_4$ 4-dimethyl pentadienyl, bis(2,4-dimethyl pentadienyl) ruthenium (RU), Ru(EtCp)(MeCp), $TiCl_4$, $WCl_5$, $WF_6$, and those precursors disclosed in commonly-owned U.S. Patent Publication No. 20090269507, titled "SELECTIVE COBALT DEPOSITION ON COPPER SURFACES."

In some embodiments, a remote plasma source 131 containing the process gases can be configured to introduce the process gases (e.g., activated process gas in plasma form including ions and radicals) into the processing chamber 100. For example, the remote plasma source can be coupled to a separate gas inlet 125 disposed at a side of the chamber body 112 for introducing the process gases directly into the inner volume 111.

The support assembly 116 includes a substrate support 132 that has a flat, or a substantially flat, substrate supporting surface for supporting the substrate 110 during processing. The substrate support 132 may be coupled to an actuator 134 by a shaft 136 which extends through a centrally-located opening formed in a bottom of the chamber body 112. The actuator 134 may be flexibly sealed to the chamber body 112 by bellows (not shown) that prevent vacuum leakage around the shaft 136. The actuator 134 allows the substrate support 132 to be moved vertically within the chamber body 112 between one or more processing positions and a loading position. The loading position is slightly below an opening of a slit valve formed in a sidewall of the chamber body 112 for loading the substrate 110 onto the substrate support 132. The processing positions can be changed as the substrate 110 is being processed.

Figure 2:
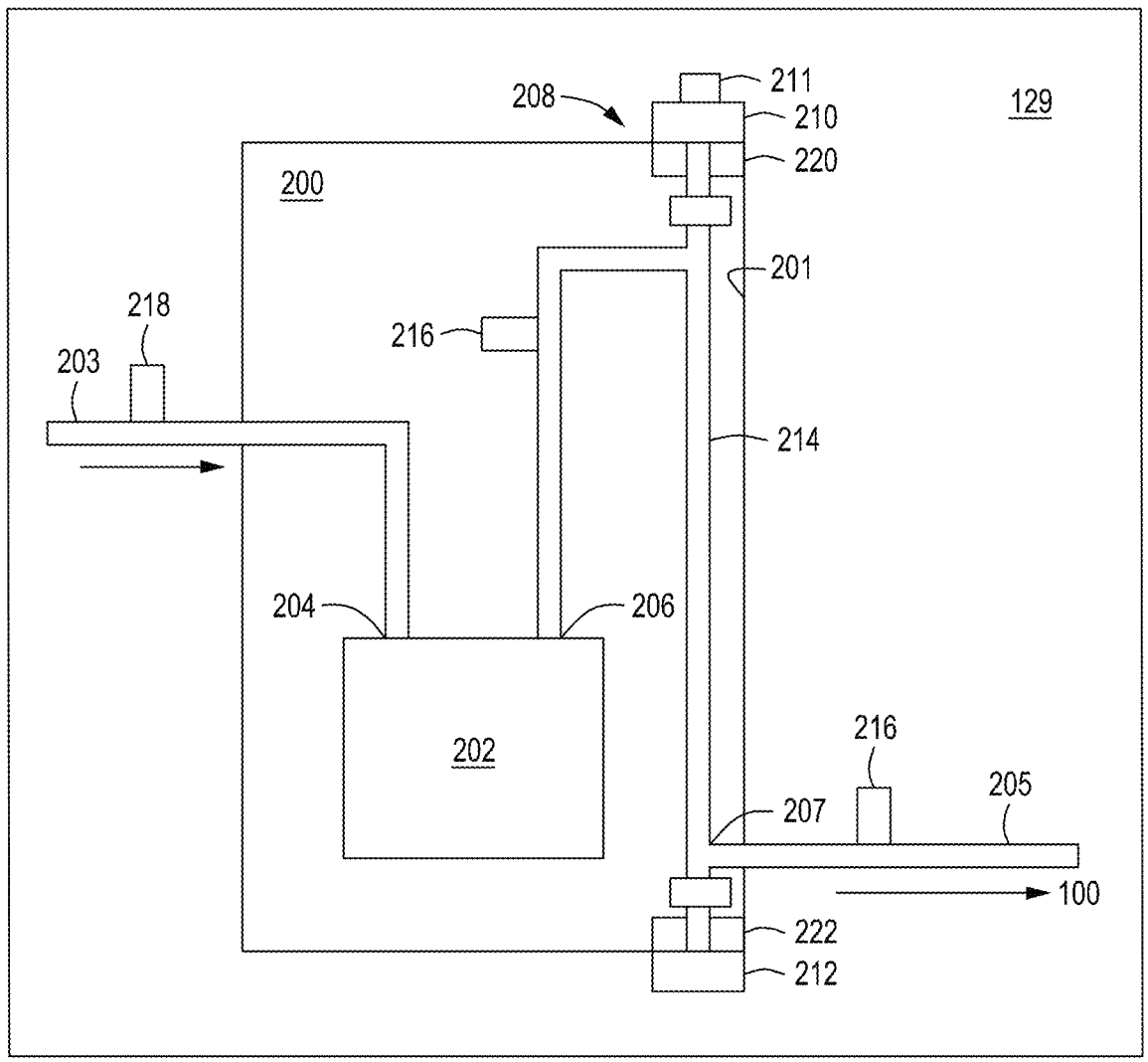
FIG. 2 is a diagram of a gas supply, in accordance with at least some embodiments of the present disclosure.

FIG. 2 is a diagram of the gas supply 129, in accordance with at least some embodiments of the present disclosure. The gas supply 129 is configured for use with a CVD process and/or an ALD process. The gas supply 129 comprises an enclosure 200 (e.g., a hot can) and an ampoule 202, which stores a precursor that is mixed with one or more process gases (e.g., carrier gas). For example, the ampoule 202 comprises an input 204 that receives a carrier gas and an output 206 that provides a mixture of the carrier gas and the precursor to the processing chamber 100.

A sensor assembly 208 is operably connected to an outside of the enclosure 200. For example, the sensor assembly 208 can be any suitable sensor capable of measuring a concentration of a precursor, such as, a Fourier Transformed IR (FTIR) sensor assembly, an NDIR sensor assembly, etc. The inventors have found that the NDIR sensor assembly is relatively inexpensive and includes simple hardware that makes the NDIR sensor assembly easy to configure for use within the enclosure 200 of the gas supply 129. Accordingly, the sensor assembly comprises a detector 210 and an infrared source 212 that are operably connected to an outside of the enclosure 200. In at least some embodiments, the infrared source 212 can be placed inside the enclosure 200, e.g., to optimize SNR. The infrared source 212 can be a filament-based board ban IR source, a semiconductor-based broad band IR source, an LED IR source, or a laser IR source. In at least some embodiments, the infrared source 212 can be an LED IR source. A gas measurement volume 214 is disposed within the enclosure 200 and along an inner wall 201 thereof. In operation, a concentration of the precursor in the mixture can be measured by the detector 210 and transmitted to a controller (e.g., the controller 102).

A first thermal insulator 220 and a second thermal insulator 222 are disposed between the enclosure 200 and the detector 210 and the infrared source 212, respectively. The first thermal insulator 220 and a second thermal insulator 222 are configured to provide insulation from the heat dissipated by the enclosure during operation (e.g., act as a thermal choke).

One or more pressure sensors can be disposed on a gas line 205 that connects to an output 207 of the sensor assembly 208 and/or a gas line 203 that connects to the input 204 of the ampoule 202. For example, in at least some embodiments, a pressure sensor 216 can be connected to the gas line 205 and a pressure sensor 218 can be connected to the gas line 203 and are configured to provide a pressure of the carrier gas in the gas line 203 and a pressure of a mixture of the carrier gas and precursor in the gas line 205, as described in greater detail below. In at least some embodiments, the pressure sensor 216 can also be connected to the gas line between the ampoule 202 the sensor assembly 208 (e.g., between the ampoule 202 and a measurement volume, described below).

FIG. 3A is a diagram of the sensor assembly 208 (e.g., an NDIR sensor assembly), in accordance with at least some embodiments of the present disclosure. In addition to the components described with respect to FIG. 2, the gas measurement volume 214 of the sensor assembly 208 comprises a chamber 302 that is configured to house one or more gases (e.g., air, carrier gas, etc.). The chamber 302 is disposed between the detector 210 and a window 304, which can be made from one or more suitable transparent materials. For example, in at least some embodiments, the window 304 can be made from glass. Similarly, a chamber 306 is disposed between the infrared source 212 and a window 308, which can be identical to the window 304. The window 304 and window 308 allow an infrared beam to be transmitted from the infrared source 212 through the gas measurement volume 214 and to the detector 210 so that the detector 210 can measure a concentration of the precursor in a mixture that comprises a carrier gas and a precursor, as will be described in greater detail below.

The detector 210 comprises at least one or more sensors. For example, in at least some embodiments, the one or more sensors can comprise a thermopile sensor 310 (e.g., a large area thermopile), a pyroelectric sensor 312, or high precision sensor 315 (e.g., a photoconductive sensor or photovoltaic sensor such as mercury cadmium telluride (MCT), InAsSb detectors, InSb detectors, InAs detectors, InGaAs detectors, or HgCdTe detectors) capable of providing a high signal-to-noise (SNR) ratio.

In at least some embodiments, the sensor assembly 208 can comprise more than one detector. For example, in at least some embodiments, a precursor detector 311a and a reference detector 311b can be placed at about 90° from each other (FIG. 3B). The precursor detector 310a and the reference detector 310b can be the same as each other or different from each other, e.g., can use the same sensors or different sensors. In at least some embodiments, the precursor detector 310a and the reference detector 310b can be identical to each other, but can use different filters (e.g., optical filters) that can be chosen to pass IR with certain wavelengths specific to a precursor and a reference. In at least some embodiments, an IR beam splitter 301 (e.g., a prism) can be used to split the IR beam into two beams, one for the precursor detector 210a (e.g., a precursor beam) and one for the reference detector 310b (e.g., a reference beam). The reference detector 310b is configured to compensate for drifts in an IR source.

In at least some embodiments, the precursor detector 310a and the reference detector 310b can be disposed in a side-by-side configuration (FIG. 3C). In such embodiments, the IR beam splitter 301 301 may be used.

With reference again to FIG. 2, as the detector 210 is located outside of the enclosure 200, the noise usually caused by the high temperatures (e.g., the ampoule temperature setpoint of about 105° C.) within the enclosure 200 does not affect measurements of the detector 210. In some embodiments, the detector 210 can be cooled (e.g., <5° C.) to increase SNR.

In at least some embodiments, a temperature sensor 211 can be coupled to the detector 210. For example, the temperature sensor 211 can be a thermistor, thermocouple, a resistance temperature detector (RTD) or other suitable temperature sensing device. The temperature sensor 211 is configured to measure a temperature of the detector 210 and/or the enclosure 200 during operation.

The detector 210 comprises at least one filter. For example, in at least some embodiments, the at least one filter comprises a first filter 314 that is configured to filter infrared light not absorbed by any gas (e.g., reference light) and a second filter 316 that is configured to filter infrared absorbed by a precursor. Thus, during operation, the detector 210 can measure a concentration of the carrier gas in a mixture and a concentration of a precursor in a mixture. The detector 210 can also comprise at least one of an operational amplifier or an analog-to-digital convertor (not shown).

Continuing with reference to FIG. 3A, the gas measurement volume 214 extends along the inner wall 201 and defines an infrared absorption path. The inventors have found that gas measurement paths of conventional sensor assemblies (e.g., about 7.5 cm in length and a total volume of about 30 cm$^3$) are limited in order to integrate the sensor assembly into the limited space in the enclosure at the output of an ampoule. The inventors have found that a gas measurement volume having a large length (e.g., increased volume) provides increased SNR for the detector 210. That is, by increasing a path length provides more gas (e.g., carrier gas and/or precursor gas) to absorb the light transmitted from an infrared source before reaching the detector. For example, the gas measurement volume can be about 0.635 cm to about 40.0 cm, e.g., 38.0 cm. For example, the inventors have found that by increasing a length of a gas measurement volume to about 40 cm (e.g., a total volume of about 160 cm$^3$ provides improved SNR for the detector 210 (e.g., five (5) times greater)), which can reduce a relative error by >2.2 factor (e.g., a 12% relative error reduced to 5% relative error) based on the volume increase, thus enabling gas concentration sensing on a level required for process control. In some embodiments, the gas measurement volume can be less than 0.635 cm and greater than 40.0 cm. Additionally, the inventors have found that a cross-section of the gas measurement volume 214 can be on the order from about 2 cm×2 cm to about 5 cm×5 cm. As can be appreciated, the length and total volume can be adjusted (e.g., increased or decreased) as required.

Figure 4:
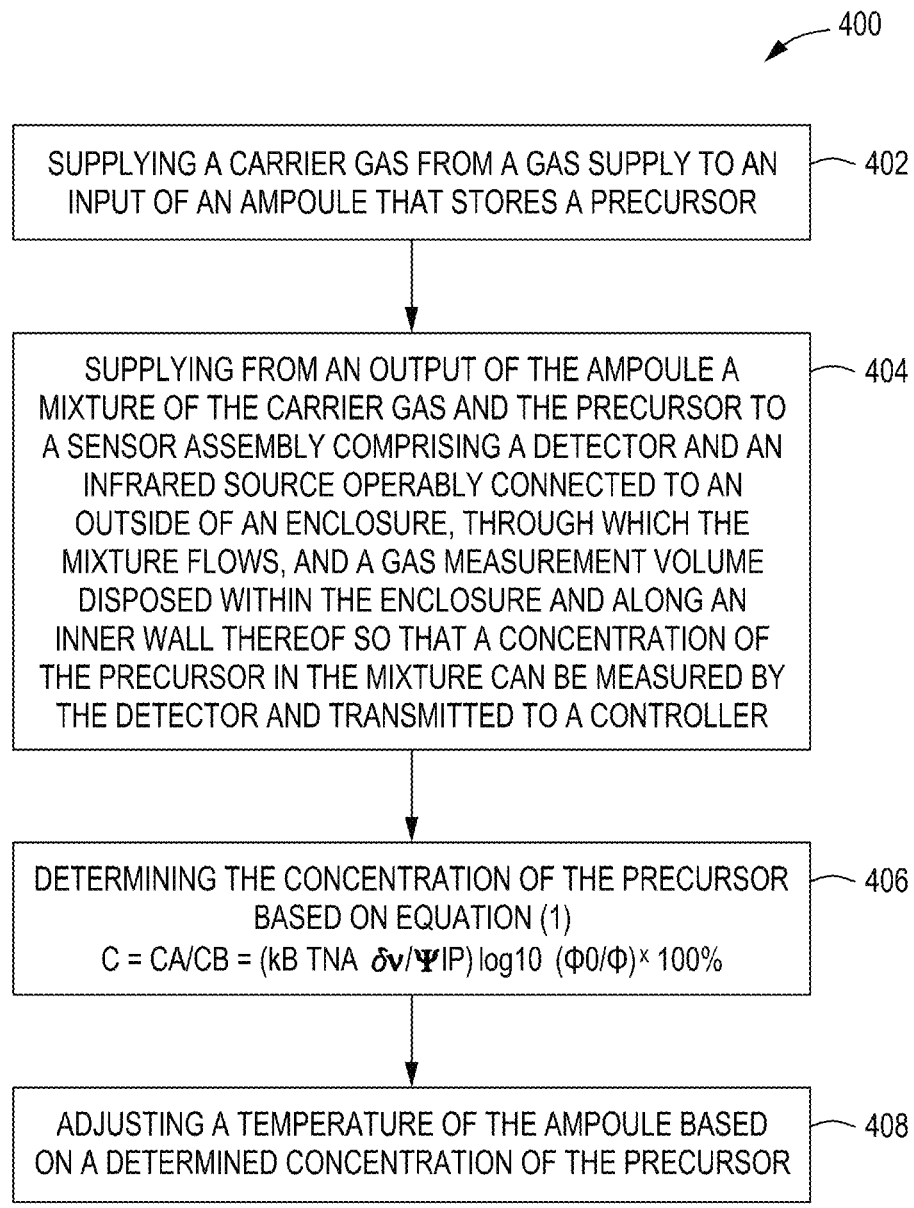
FIG. 4 is a flowchart of a method of processing a substrate, in accordance with at least some embodiments of the present disclosure.

FIG. 4 is a flowchart of a method 400 of processing a substrate, in accordance with at least some embodiments of the present disclosure. For example, the method 400, at 402, comprises supplying a carrier gas from a gas supply to an input of an ampoule that stores a precursor. For example, the gas supply 129 can supply one or more of the above-described carrier gases to the ampoule 202. In at least some embodiments, the carrier gas can be argon (or other noble gas). Likewise, the precursor can be one or more of the above-described precursors, such as pentakis (dimethylamino) tantalum (V)—Ta (NMe$_2$)$_5$ or tetrakis (dimethylamino) titanium ($C_8H_{24}N_4Ti$).

Next, at 404, the method 400 comprises supplying from an output of the ampoule a mixture of the carrier gas and the precursor to a sensor assembly (e.g., the sensor assembly 208. As noted above, the sensor assembly 208 comprises a detector and an infrared source operably connected to an outside of an enclosure, through which the mixture flows, and a gas measurement volume disposed within the enclosure and along an inner wall thereof so that a concentration of the precursor in the mixture can be measured by the detector and transmitted to a controller. Alternatively or additionally, as noted above, in at least some embodiments, the infrared source can be placed inside the enclosure.

Next, at 406, the method 400 comprises determining a concentration of the precursor based on the Equation (1):

$$C = C_A/C_B = (k_B T N_A \delta\nu/\Psi l P)\log_{10}(\phi_0/\phi) \times 100\%, \quad (1)$$

where C=concentration of A in B [Abs], $C_A$=concentration of A [mol/m$^3$], $C_B$=concentration of B [mol/m$^3$], $K_B$=Boltzmann Constant [J/K], T=Temperature [K], $N_A$=Avogadro's Number [#/mol], $\Psi$=Integrated Molar Absorptivity [m/mol], l=IR Source Path Length, [m], P=Total Pressure [Pa], $\phi_0$=Photodiode Signal without A, $\phi$=Photodiode Signal with A, and $\delta\nu$=spectral width of filter [m$^{-1}$]. The pressure for mixture of the carrier and the precursor. In Equation (1), the total pressure is the pressure of the mixture of the carrier gas and the precursor in the gas line 205. The detector 210 transmits a measurement of an absorptivity of the precursor and the pressure sensor 216 transmits a detected pressure of the mixture of the carrier and the precursor to the controller 102, which, in turn, uses Equation (1) to determine a concentration of the precursor.

Next, at 408, the method 400 comprises adjusting a temperature of the enclosure based on a determined concentration of the precursor. For example, the controller 102 can adjust a temperature of the ampoule 202. For example, in at least some embodiments, when the determined concentration of the precursor falls below a predetermined value, the controller 102 increases a temperature of the ampoule 202 to increase evaporation of the precursor stored in the ampoule 202, which, in turn, increases a concentration of the precursor. In at least some embodiments, such as when there is temperature overshoot at the ampoule, the controller 102 can be configured to decrease a temperature of the ampoule.

While the foregoing is directed to embodiments of the present disclosure, other and further embodiments of the disclosure may be devised without departing from the basic scope thereof.

The invention claimed is:

1. A gas supply configured for use with a processing chamber, comprising:
   a heated enclosure;
   an ampoule disposed within the enclosure and configured to store a precursor, the ampoule comprising an input to receive a carrier gas and an output to provide a mixture of the carrier gas and the precursor through a non-dispersive infrared sensor assembly to the processing chamber;
   the non-dispersive infrared sensor assembly comprising a gas measurement volume disposed within the heated enclosure and along an inner wall thereof defining an infrared absorption path having a path length greater than or equal to about 38 cm,
   a sensor assembly comprising a detector and an infrared source each operably connected to and located outside of the heated enclosure so that a concentration of the precursor in the mixture flowing through the gas measurement volume disposed within the heated enclosure can be measured by the detector and transmitted to a controller.

2. The gas supply of claim 1, further comprising at least one pressure sensor connected to a gas line that connects to an output of the sensor assembly or a gas line that connects to the input of the ampoule.

3. The gas supply of claim 1, wherein the precursor is an alkylamide precursor.

4. The gas supply of claim 3, wherein the alkylamide precursor comprises pentakis (dimethylamino) tantalum (V)—Ta (NMe$_2$)$_5$ or tetrakis (dimethylamino) titanium ($C_8H_{24}N_4Ti$).

5. The gas supply of claim 1, wherein the carrier gas is an inert gas.

6. The gas supply of claim 5, wherein the inert gas is a noble gas.

7. The gas supply of claim 1, wherein the detector comprises at least one of a thermopile sensor, a pyroelectric sensor, a photoconductive sensor, or
   a photovoltaic sensor.

8. The gas supply of claim 7, wherein the detector comprises at least one of an operational amplifier or an analog-to-digital converter.

9. The gas supply of claim 1, wherein the detector comprises at least one optical filter.

10. The gas supply of claim 9, wherein the at least one optical filter comprises a first filter configured to filter infrared light not absorbed by any gas and a second filter configured to filter infrared light absorbed by the precursor.

11. The gas supply of claim 1, wherein the gas supply is configured for use with at least one of a chemical vapor deposition chamber or an atomic layer deposition chamber.

12. The gas supply of claim 1, wherein the gas measurement volume has a length of greater than or equal to about 40.0 cm.

13. The gas supply of claim 1, wherein a first thermal insulator and a second thermal insulator are disposed between the enclosure and the detector and the infrared source, respectively.

14. A system for processing a substrate, comprising:
a processing chamber; and
the gas supply of claim 1 operably coupled to the processing chamber.

15. The system of claim 14, further comprising a pressure sensor connected to an output of the non-dispersive infrared sensor assembly.

16. The system of claim 14, wherein the precursor is an alkylamide precursor.

17. A gas supply configured for use with a processing chamber, comprising:
a heated enclosure;
an ampoule disposed within the enclosure and configured to store a precursor, the ampoule comprising an input to receive a carrier gas and an output to provide a mixture of the carrier gas and the precursor through a non-dispersive infrared sensor assembly to the processing chamber;
the non-dispersive infrared sensor assembly comprising a sensor assembly comprising a precursor detector and a reference detector, an infrared beam splitter configured to split an infrared beam from an infrared source into a precursor beam and a reference beam, the precursor beam directed at the precursor detector through a gas measurement volume, wherein the gas measurement volume is disposed within the heated enclosure and along an inner wall thereof, defining an infrared absorption path having a path length greater than or equal to about 38 cm, and the reference beam directed at the reference detector;
wherein each of the precursor detector and the reference detector comprise at least one of a thermopile sensor, a photoconductive sensor, a photovoltaic sensor, or a pyroelectric sensor and wherein the infrared source, the precursor detector, and the reference detector are operably connected to, and located outside of, the heated enclosure and configured such that a concentration of the precursor in the mixture flowing through the gas measurement volume disposed within the heated enclosure can be measured by the precursor detector and transmitted to a controller.

* * * * *